(12) United States Patent
Forsell

(10) Patent No.: US 8,460,938 B2
(45) Date of Patent: Jun. 11, 2013

(54) BLOOD VISCOSITY ANALYSIS

(76) Inventor: Tommy Forsell, Uppsala (SE)

( * ) Notice: Subject to any disclaimer, the term of this patent is extended or adjusted under 35 U.S.C. 154(b) by 282 days.

(21) Appl. No.: 12/935,635

(22) PCT Filed: Mar. 31, 2009

(86) PCT No.: PCT/SE2009/050339
§ 371 (c)(1),
(2), (4) Date: Nov. 23, 2010

(87) PCT Pub. No.: WO2009/123555
PCT Pub. Date: Oct. 8, 2009

(65) Prior Publication Data
US 2011/0104738 A1 May 5, 2011

(30) Foreign Application Priority Data
Apr. 1, 2008 (SE) ........................ 0800724

(51) Int. Cl.
| | |
|---|---|
| G01N 33/86 | (2006.01) |
| G01N 33/72 | (2006.01) |
| G01N 21/00 | (2006.01) |
| G01N 21/75 | (2006.01) |
| G01N 15/06 | (2006.01) |
| G01N 33/00 | (2006.01) |
| G01N 33/48 | (2006.01) |
| G01N 11/00 | (2006.01) |
| G01N 37/00 | (2006.01) |

(52) U.S. Cl.
USPC ........... 436/69; 422/68.1; 422/73; 422/82.05; 436/66; 436/164; 73/54.01; 73/64.41; 73/64.43

(58) Field of Classification Search
USPC .............................. 422/73; 436/66; 73/64.43
See application file for complete search history.

(56) References Cited

U.S. PATENT DOCUMENTS

| | | | |
|---|---|---|---|
| 4,034,601 A | 7/1977 | Geiger | |
| 5,197,017 A | 3/1993 | Carroll et al. | |
| 6,197,494 B1 * | 3/2001 | Oberhardt | 435/4 |
| 7,437,913 B2 * | 10/2008 | Djennati et al. | 73/64.41 |
| 7,760,340 B2 * | 7/2010 | Hoshiko et al. | 356/39 |
| 2004/0214337 A1 | 10/2004 | Kautzky | |
| 2009/0221011 A1 * | 9/2009 | Stiene et al. | 435/13 |

FOREIGN PATENT DOCUMENTS

| | | |
|---|---|---|
| EP | 0 394 070 A1 | 10/1990 |
| WO | WO99/47907 | 9/1999 |
| WO | WO2004/109277 A1 | 12/2004 |
| WO | WO2006/104451 A1 | 10/2006 |
| WO | WO2007/101993 A2 | 9/2007 |

* cited by examiner

*Primary Examiner* — Jill Warden
*Assistant Examiner* — Charles D Hammond
(74) *Attorney, Agent, or Firm* — Birch, Stewart, Kolasch & Birch, LLP

(57) ABSTRACT

A blood analyzing device (100) comprises a holder (110) for receiving a cuvette (20) with a blood sample (30). The device (100) induces a movement of the blood cells in the sample (30) by applying a field (230) over the cuvette (20). A detector (130) detects, based on output light from the blood sample (30) originating from a light source (120), a change in the induced movement of the cells caused by an increase in viscosity of the blood due to an aggregation and/or coagulation process. A processor (140) processes the detector reading and generates a signal representative of the hemostasis function of the tested blood.

27 Claims, 11 Drawing Sheets

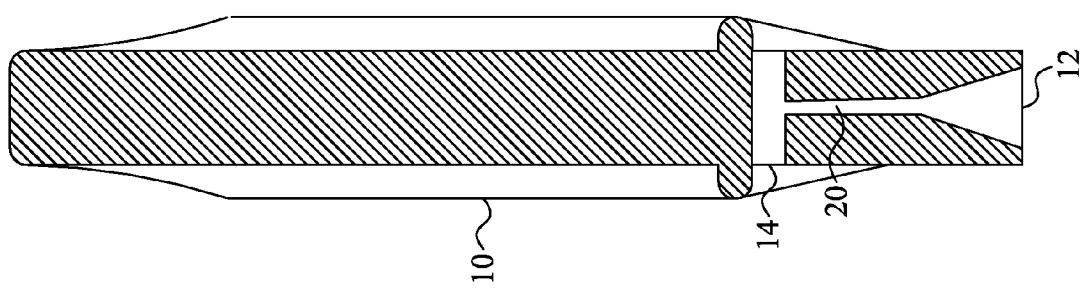
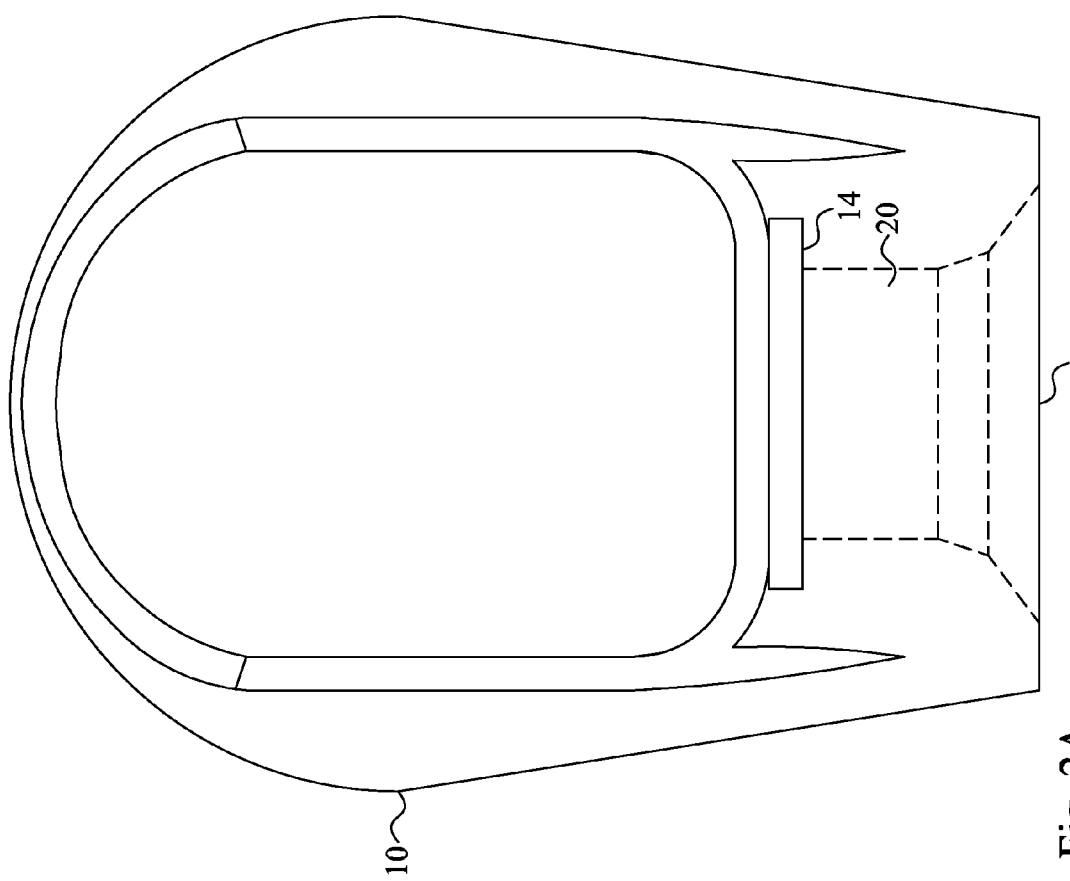
Fig. 2A
Fig. 2B

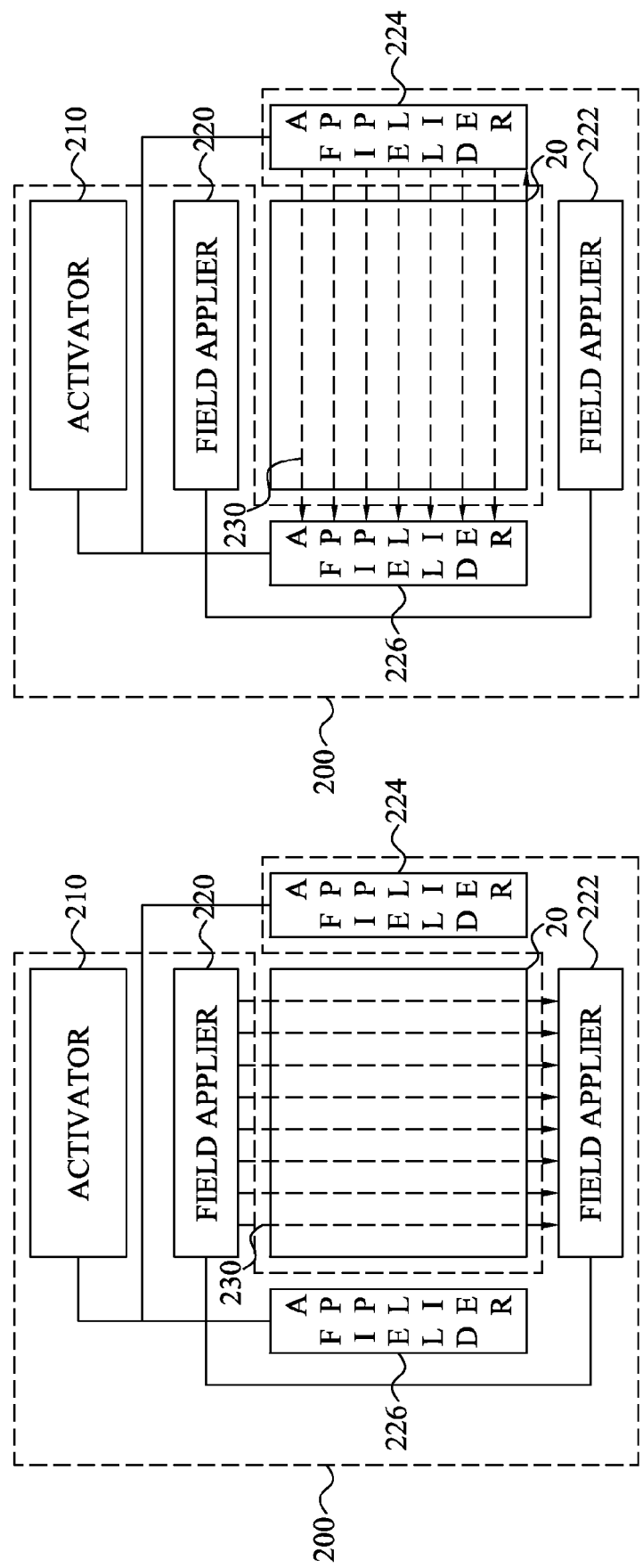

BLOOD VISCOSITY ANALYSIS

TECHNICAL FIELD

The present invention generally relates to blood analysis, and in particular to a blood analyzing device capable of monitoring viscosity-changing procedures in a blood sample and uses thereof.

BACKGROUND

Blood is commonly described as a complex red fluid consisting of plasma with a suspension of blood cells, mainly red blood cells. In an adult the blood volume is approximately 5 liters, of which 40-50% is red blood cells. The ratio between red cells and plasma is called hematocrit. Plasma consists mainly of water with proteins, sugar, vitamins, hormones, etc. A red blood cell, or erythrocyte, consists of a thin membrane as a kind of balloon in which there is water and a high concentration of the protein hemoglobin (Hb) in various forms. Hemoglobin is a complex molecule containing heme groups with iron atoms that can bind to and release oxygen and carbon dioxide in the circulation. Normally there is approximately 13-15 g hemoglobin per 100 ml blood in an adult, corresponding to 4-5 million red blood cells. Even a very small sample of blood taken from one person is a representative amount of blood cells for making measurements to determine certain properties and conditions of the blood. The hemoglobin value is a representation of the oxygen transportation capacity of the blood to other tissue and a parameter for patient diagnosis. Hemoglobin value is furthermore a primary safety and quality parameter in blood banking where blood is stored for transfusion purposes and collected as raw material for blood based industrial purposes.

Hemoglobin measurement is one of the most common diagnostic tests in the world today. Recently, development has taken place in the field of hemoglobin measurement, in that whole blood can be used as measurement material, thereby relaxing the need for hemolysation. An example of such an improved hemoglobin measuring device is disclosed in the International patent application number WO 2006/104451.

In addition to determining hemoglobin in a blood sample, other blood tests are routinely employed in primary care diagnosis. An example of such additional test is bleeding time tests. This test measures the time it takes for small blood vessels to close off and bleeding to stop and is performed to asses the platelet function of a patient. The Ivy method is the traditional procedure for testing bleeding time. The test involves inflating a sphygmomanometer to 40 mm Hg around the upper arm of the patient. A 5 mm deep incision is made with a special tool on the flexor surface of the forearm and the time is measured to cessation of bleeding. Every 30 seconds filter paper is used to draw off the blood.

The Ivy test is a rather unreliable test as several external factors can affect the test results, such as thickness of patient skin, ambient temperature, pressure applied when cutting skin, etc. In addition, the Ivy test can primarily only be utilized for detecting whether there are some problems with the platelet function in patient but is of little use for quantifying the platelet function of a patient.

WO 2004/109277 discloses an apparatus for determining the coagulation status in a blood or plasma sample. Magnetic particles added to the blood or plasma sample are caused to move through the sample by application of a magnetic field. Magnetic field sensors register changes in the response of the magnetic particles to the applied magnetic field and the coagulation status of the sample can be determined.

WO 2004/093641 discloses an acoustic blood analyzer with a transducer section of acoustic biosensors for measurement of blood coagulation in a sample. Acousto-mechanical sensors generate acoustic waves that penetrate the blood sample. As the blood coagulates on the sensors their mechanical properties change, resulting in measurable changes in the sensor natural frequency and power attenuation.

SUMMARY

There is a need for a simple, fast and reliable test for monitoring viscosity changes in a small blood sample due to thrombocyte aggregation and/or coagulation.

It is a general object of the present invention to provide a hemostasis analysis of a small blood sample.

It is another object of the invention to provide a blood analyzing device for assessing aggregation and/or coagulation efficiency of a small blood sample.

These and other objects are met by the invention as defined by the accompanying patent claims.

Briefly, the present invention involves a blood analyzing device comprising a holder arranged for receiving and supporting a container having a cuvette filled with a small volume blood sample. The device comprises inducing means arranged in connection with the cuvette for inducing a movement of the blood cells in the sample. The inducing means preferably comprises field appliers for applying a field, such as electric, magnetic or acoustic field, over at least a portion of the blood sample to thereby directly or indirectly affect the blood cells and induce a movement thereof in the sample.

A light source is arranged for providing input light into the blood sample. A detector is arranged in the analyzing device for monitoring the movement of the blood cells and detects a change in the induced movement of the blood cells caused by a blood viscosity increase due to an aggregation and/or coagulation process. The detector performs this detection based on output light from the blood sample. The detector readings are processed by a processor for the purpose of generating at least one hemostasis parameter that is representative of the aggregation function, such as thrombocyte activity, and/or coagulation function, such as coagulation efficiency.

The blood analyzing device can preferably be used for both assessing the aggregation function and the coagulation function of hemostasis. In such a case, a first field strength is first employed for inducing blood cells movement until the aggregation process increases the viscosity to a level that results in a detectable movement change. The field strengths can then be increased to a second level to once more induce movement of the (at least partly aggregated) blood cells until the coagulation process increases the blood viscosity even further. In such a case, the processor can generate both an aggregation representing parameter and a coagulation representing parameter.

An electric field can be used by the blood analyzing device for inducing movement of the blood cells by acting upon negative charges present on the cell surface. Alternatively, at least one ferromagnetic object, such as iron filings, can be added to the blood sample or be present in the cuvette. Electromagnets positioned around the cuvette are selectively activated to move the ferromagnetic objects and also blood cells attached or connected thereto in the blood sample. A further example includes the usage of (ultrasound) transducers that are able to transmit acoustic waves into the sample to thereby move the blood cells present therein.

The present invention also relates to a method of analyzing a blood sample in vitro.

BRIEF DESCRIPTION OF THE DRAWINGS

The invention together with further objects and advantages thereof, may best be understood by making reference to the following description taken together with the accompanying drawings, in which:

FIG. 2A is a schematic front view of a sample container that can be used in the blood analyzing device according to the present invention;

FIG. 2B is a cross-sectional view of the sample container of FIG. 2A along the line A-A;

FIGS. 4A to 4D are schematic block diagrams of a movement inducing arrangement according to another embodiment of the present invention;

DETAILED DESCRIPTION

Figure 1:
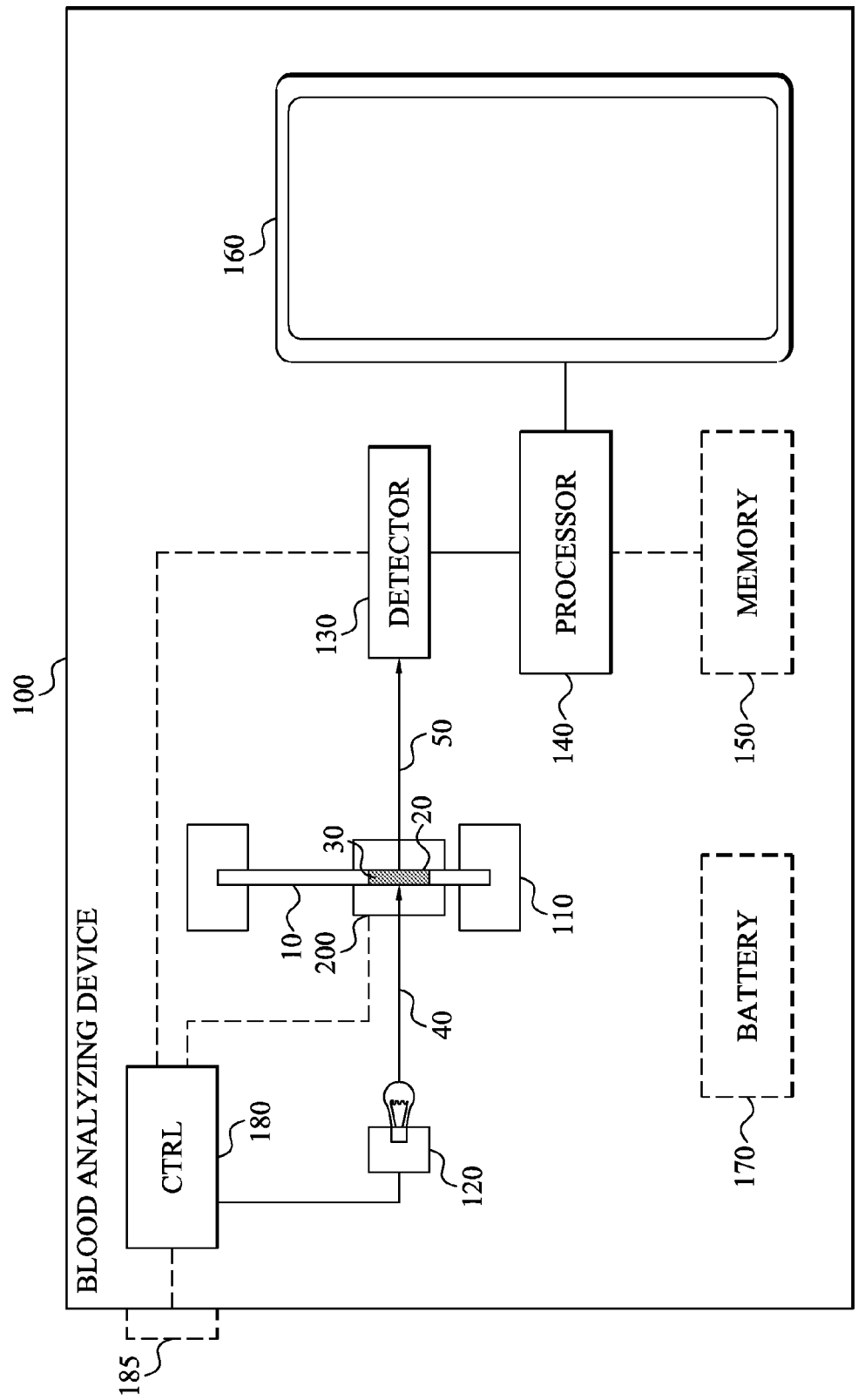
FIG. 1 is a schematic block diagram of an embodiment of a blood analyzing device according to the present invention.

Throughout the drawings, the same reference characters will be used for corresponding or similar elements.

The present invention generally relates to blood analysis, and in particular to a blood analyzing device and method capable of monitoring viscosity-affecting hemostasis procedures in a blood sample. The device of the present invention is particularly advantageous for assessing one or more blood processes in vitro occurring during and in connection with hemostasis.

Hemostasis is a complex process involving a multitude of cells and coagulation factors and can be initiated according to different pathways. In a simplistic disclosure, hemostasis can be divided into three main sub-processes: 1) aggregation or pro-coagulation, 2) coagulation by formation of fibrin network, and 3) final formation of a blood clot.

The first sub-process, aggregation, is triggered when platelets, also denoted as thrombocytes, circulating in the blood come into contact with collagen, which is exposed when the endothelial blood vessel lining is damaged. The platelets bind to the collagen with surface collagen-specific glycoprotein Ia/IIa receptor. The platelets are then activated and release the contents of their granules into the plasma. This content comprises different coagulation factors and platelet activating factors, in turn activating other platelets. The platelets also adhere to each other via their adhesion receptors or integrins, typically via fibrinogen links. The aggregation process therefore leads to an initial network of thrombocyte threads.

The released coagulation factors are involved in the second hemostasis stage; coagulation or blood clotting. There are generally two different pathways of the coagulation cascade, the contact activation pathway (formerly known as intrinsic pathway) and the tissue factor pathway (formerly known as the extrinsic pathway). The two pathways utilize different coagulation factors but ultimately end at a common pathway, generating thrombin from prothrombin causing the formation of fibrin from its precursor fibrinogen. The fibrin protein threads enforce the initial network and form, together with the platelets, a haemostatic plug or blood clot.

In the third sub-process, the high concentration of myosin and actin filaments in the platelets are stimulated to contract pulling or tying together the fibrin threads to a very strong plug that closes the damaged blood vessel.

Each of these steps is of vital interest and the previously mentioned Ivory test is a general screen test for the coagulation test. Ivory test is an artificial introduction of a wound in the skin and then using the blood itself as marker for the process, which is simply measured in time.

The three sub-processes of hemostasis cause a change, i.e. rise, in the viscosity of the blood, which is detectable according to the present invention. In order to assess a patient's hemostasis and bleeding response, a blood analyzing device should be able to monitor and assess at least one of the sub-processes and preferably multiple or all sub-processes.

The present invention aims to standardize the Ivory test method by eliminating the error sources, briefly mentioned in the background section. According to the invention, the sample is preferably taken as a capillary test with the causing of a wound as the starting point of the process. An amount of blood is then drawn into a cavity, agitated and measured, preferably continuously, periodically or intermittently, measured for the red blood cells until the movement caused by the agitation stops at the first step of the procedure, i.e. aggregation. This gives a standardized measurement of thrombocyte activity. If the agitation is amplified, the movement can be followed to the next step, blood clotting. The strength of the clot may then be measured by further enforcement of the agitation.

FIG. 1 is a schematic block diagram of a blood analyzing device 100 according to the present invention adapted for monitoring hemostasis and coagulation in a blood sample.

A sample container 10 having a cuvette 20 containing a blood sample 30 is introduced in a holder 110 of the device 100. The cuvette 20 is generally in the form of a so-called microcuvette in that the total size of the container 10 and the blood sample 30 is very small. FIG. 2A is a frontal view of an example of a sample container 10 that can be used according to the present invention. FIG. 2B is a cross-sectional view of the sample container 10 taken along the line A-A.

The container 10 comprises a cuvette 20 designed for containing the blood sample to be analyzed by the blood analyzing device. An end side of the container 10 comprises an opening 12 that is contacted with blood, causing the blood, through the capillary effect, to enter the container 10 and fill up the cuvette 20. The container 10 preferably also comprises an air outlet 14 allowing air present in the cuvette 20 to escape, when blood is being drawn into the container 10. The cross-sectional view of the container 10 more clearly illustrates the opening 12 and how it is in contact with the cuvette 20.

The blood analyzing device of the present invention is however not limited to usage with sample container as illustrated in FIGS. 2A and 2B but can be used in connection with other container and cuvette designs. Generally the container could have a size of one up to a few square centimeters. The cuvette is generally in the form of a rectangular parallelepiped box (cuboid) or a cylinder, though other forms are still possible. The height and width of the cuvette could, for instance, be in the range of 1-10 mm, such as about 5 mm. The thickness could be about 0.01-1 mm, such as about 0.05-0.5 mm. A total volume of the cuvette is typically in the range of 1-10 µl.

In some applications it can be preferred to actively induce or enhance aggregation and coagulation in the blood sample of the cuvette. In such a case an aggregation and/or coagulation trigger substance or a mixture thereof can be added to the blood sample prior, during or after filling the cuvette. Examples of such substances are well known in the art and include, for instance, collagen and adrenaline. The cuvette and/or the entrance channel to the cuvette can alternatively, or in addition, be pre-coated with such substances, thereby promoting aggregation and/or coagulation in the blood as it is drawn into the cuvette.

The blood analyzing device 100 also comprises a unit or means 200 for inducing a movement of blood cells in the sample 30 when the container is positioned in the holder 110. The inducing means 200 preferably comprises field applying means that directly or indirectly, which is described further herein, affects and agitates at least the blood cells present in the cuvette 20 to thereby induce a movement of the cells inside the cuvette 20.

A detector 130 is arranged for detecting a change in the induced movement of the blood cells in the sample 30 arising from a change in the viscosity of the blood sample 30. Furthermore, this viscosity change that is detectable by the detector 130 through a change in the movement pattern of the blood cells is caused by the sub-processes of coagulation and hemostasis described above.

The detector 130 also generates a detection signal based on the detected change in the induced movement. This detection signal is forwarded to a connected processor 140 that is utilized by the device 100 for monitoring the hemostasis/coagulation process in the blood sample 30 through a viscosity change in the blood sample 30 as determined based on the detection signal.

The processor 140 preferably has access to an algorithm or conversion/mapping function that is employed for calculating a viscosity representing value based on the provided input data, i.e., detection signal. Alternatively, the processor 140 can have access to a standardized table, standard curve or database of standard viscosity values and corresponding detector values. Thus, such a table/curve/database can then be used for mapping a collected detector value to a viscosity representing value.

Once the processor 140 has determined a viscosity representing value of the current blood sample, the result can be presented on a display screen 160 of the device 100 for review of a user, e.g., a physician, other medical personnel or indeed the patient himself/herself. In addition, to merely displaying a viscosity value, the processor can be arranged for comparing the determined viscosity values with normal viscosity values. The normal values could be an average viscosity representation for the general population. In the case of a large difference between the determined value and the normal range, the processor can display an alarm alert on the display screen 160, for example if the viscosity value is lower than normal. The display screen 160 can also display a normal indication if the measured value is within the normal viscosity range, display a high indication if the measured value exceeds the normal range and display a low indication if the measured value falls below the normal range.

The processor 140 can also or instead store the determined viscosity value in a connected memory 150 for display or retrieval at a later time. If the blood analyzing device 100 comprises or can be connected to a communication unit, possibly a wireless communication unit, the determined viscosity value can be sent from the device 100 to a remote location, e.g., a physician's office.

The detector 130 can be implemented as a simple camera unit that merely monitors the induced movement of the (red) blood cells and generates the detection signal upon detection of a significant change, i.e., reduction, in the induced movement. The detection signal can then be a representation of the time period from the start of the monitoring procedure, such as the start from the application of the induced movement by the inducing means 200 or the positioning of the sample container 10 into the holder 110, up to detection of the significant change in induced movement.

Generally, when introducing the fresh blood sample 30 and container 10 into the holder 110 and when inducing movement of the blood cells, the blood cells move relatively freely. However, as coagulation is triggered and proceeds in the sample due to the presence of aggregation and coagulation triggering substances, platelets in the blood sample 30 aggregate thereby impeding the free movement of the blood samples, causing an increase in blood viscosity. The aggregation process is a cascade-like process, where activated platelets trigger and activate other platelets. As a consequence, the change in viscosity due to aggregation of blood cells in the sample 30 occurs rather suddenly once enough platelets have become activated. This period in time can easily be detected by the detector 130.

According to the invention, the blood analyzing device 100 also comprises a light source 120 arranged for providing input light 40 into the blood sample 30 present in the cuvette 20. The detector 130 is thereby arranged for detecting the change in induced movement of the blood cells based on output light 50 from the blood sample.

The light source 120 could be a monochromatic light source providing light at a wavelength causing a high absorbance of hemoglobin in the red blood cells in the blood sample 30. Thus, the wavelength could be a wavelength for which one of the hemoglobin species or bilirubin in the red blood cells has maximum absorbance. The detector 130 can then be a general photometer that can detect the absorbance, transmittance or reflectance at that particular wavelength. Hemoglobin can be present in one of the multiple species. In the art, the main such Hb species are oxyhemoglobin ($HbO_2$), carboxyhemoglobin (HbCO), methemoglobin or hemoglobin (Hi), reduced hemoglobin (Hb) and sulfhemoglobin (SHb). Generally, SHb has maximum absorbance close to 625 nm, $HbO_2$ close to 540 nm and 577 nm, HbCO close to 538 nm and 570 nm, Hb close to 555 nm and Hi close to 500 nm. The light provided by the light source 120 may therefore be selected to be close to any of these maximum absorbance wavelengths.

However, it might also be advantageous to have a reference wavelength or using multiple wavelengths in order to provide a more accurate detection of the change in induced movement. For example, the light source 120 could be a broad band light source, providing white light, preferably with a continuous wave length spectrum within the whole or part of the wavelength range 350 to 900 nm. The detector 130 could then be in the form of a spectrophotometer registering the light intensity of the output light as a function of wavelength. A possible implementation of such a detector 130 is a monolithic multi-wavelengths diode array.

Alternatively, the light source 120 could be a variable wavelength monochromatic light source being able to provide in a sequence of multiple separate wavelengths, preferably in the range of 350 to 900 nm. The detector 130 could then be a standard photometer registering absorbance, transmittance or reflectance of the output light 50.

The present invention can be used in connection with different known light source embodiments 120 including, but not limited to, LED, laser and flash types.

The detector 130 can be arranged for performing detection/measurements on output light 50 having passed through the blood sample 30 in the cuvette 20. Thus, the detector 130 could then detect absorbance/transmittance at one or more wavelengths in the output light 50. Alternatively, the detector 130 can be arranged for detecting reflected output light 50 from the measuring volume 32 of the sample 30. In such a case, the detector 130 preferably detects a significant change in the induced movement as a significant change in absorbance/transmittance at one or more wavelengths at a particular portion of the blood sample 30. Thus in this embodiment, the detector 130 preferably has an extended detection area, typically consisting of independent detection elements, for independently detecting and monitoring absorbance/transmittance changes at different portions of the cuvette 20. In such a case, different light guides (not illustrated) can be arranged between the cuvette 20 and the detector 130 for directing output light 50 originating from different cuvette/sample portions to different detector elements.

However, for most practical implementations, spectrophotometric measurements at selected wavelengths are not necessary for the detector 130 in order to monitor and detect changes in the induced movement of the blood cells in the sample 30. Thus, any detector embodiments 130, with or without usage of a light source 120, that are able to monitor such movement changes can be used and are encompassed by the present invention. It is therefore enough for being able to detect an accumulation of blood cells, in particular red blood cells and platelets, in a portion of the cuvette 20 due to the aggregation process.

Initially, the red blood cells are fairly homogenously distributed in the blood sample 30 in the container 10. Consequently, the distribution of detectable hemoglobin is initially fairly homogenous. However, as the hemostasis is proceeding in the blood sample 30, the red blood cells will aggregate into larger complexes as previously described. Consequently, the blood sample 30 in the container 10 will then include larger parts of high hemoglobin concentration, i.e., aggregated red blood cells, present in the remaining portion of the blood sample having comparatively lower concentration of red blood cells and hemoglobin.

When the inducing means 200 induces a movement of the blood cells, these aggregates will be set into motion through the blood sample 30 in the container 10. Generally, the detector 130 preferably only performs detection of output light from a detection volume constituting a sub-portion of the whole blood sample volume in the container 10. In such a case, the blood cell aggregates are moved through the detection volume due to the induced movement. As a consequence, the detector 130 registers alternating changes in the output light detection as high absorbing hemoglobin molecules are moving through the detection volume. Thus, when a blood cell aggregate is present in the detection volume, the local high concentration of hemoglobin in the aggregates will be detected as an increase in the absorbance for the wavelength/wavelengths, where hemoglobin has maximum absorbance. Shortly thereafter, the induced movement brings the blood cell aggregate away from the detection volume, resulting in a sharp drop in the absorbance at this/these wavelength/wavelengths.

As the hemostasis proceeds, the inducing means 200 is no longer capable of freely moving the blood cells aggregates through the blood sample 30. The detector 130 will detect this as reduction in the speed or rate of alternation between high and low absorbance for the hemoglobin wavelength/wavelengths. Actually, the movement of the blood cell aggregates may actually stop at one point, thereby the detector 130 will get substantially a single detector reading as there is not longer any significant change in the hemoglobin concentration in the detection volume.

The blood analyzing device 100 consequently preferably uses the red blood cells, or more correctly the hemoglobin, as a tracer or indicator in order to follow the progress of hemostasis and the reduced freedom of movement of the red blood cells as the hemostasis proceeds in the blood sample 30.

The blood analyzing device 100 typically also comprises a battery 170 or some other power source, providing the power required for operating the other including elements of the device 100. It is anticipated by the present invention that the battery 170 can be replaced by an external power source, connected to the device 100 through a power cord.

The measurement of the blood analyzing device 100 could be started automatically once the sample container 10 has been placed in the holder 110 or once the container 10. In such a case, a control unit 180 switches on the inducing means 110 and selectively activates the detector 130 when a predefined time period has elapsed from the container positioning. The measurement is then started after a predefined period of time for allowing the aggregation to start or at least proceed slightly before the monitoring of the detector is initiated.

Instead of having an automatic initiation of the measurements, the blood analyzing device 100 can be equipped with an activation input 185, non-limitedly illustrated in the form of a push button 185 in the figure. The user of the device 100 activates the input 185, which causes the generation of an activation signal that is forwarded to the controller 180. The controller 180 activates the inducing means 110, the detector 130 and the light source 120 for performing a viscosity reading in the blood sample 30.

In one preferred approach, the blood analyzing device 100 is configured for performing multiple measurements at multiple different time instances to thereby get a monitoring of the change in induced movement. For example, a separate detection can be performed every second, every 2nd second, every 5th second, every 10th second, every 20th second, every 30th second or every minute in a time frame of up to, for instance, 1 minute, 2 minutes, 3 minutes, 4 minutes, 5 minutes, 6 minutes, 7 minutes, 8 minutes, 9 minutes or 10 minutes.

The processor 140 can use all of these multiple detector readings or at least a portion therefore in the determination of the coagulation representing parameter of the blood sample 30.

In a preferred embodiment of the present invention, the blood analyzing device 100 is able to analyze not only the hemostasis in the blood sample 30 but can also perform hemoglobin (Hb) measurements in the sample 30.

A preferred approach is to first perform Hb measurements and then perform the hemostasis measurement. In such a case, the light detector 130 is arranged for detecting, at least once within a measuring time interval following positioning of the container 10 in the holder 110, output light 50 having passed through the blood sample 30. The input light 40 is allowed to pass through the sample 30 in the comparatively shorter extension of the cuvette 20.

Thus, for Hb measurement the detector 130 determines the absorbance or transmittance at different wavelengths (or frequencies) in the output light 50. The light source 120 can have the same settings as for coagulation measurements, e.g. provide light over a whole wavelength spectrum (white light) or sequentially provide monochromatic light at different wavelengths. In the latter case, the separate wavelengths preferably correspond to the wavelengths of maximum absorbance for the different Hb species.

The processor 140 will then process the measurement results for the purpose of determining the total Hb concentration (amount) in the blood sample 30 and/or at least one Hb fraction.

The Hb measurements are preferably conducted with a blood sample 30 that is homogenous or close to homogenous.

The viscosity value of a blood sample depends, if the movement of red blood cells is monitored by the detector 130, at least to some extent, on the number of red blood cells or the Hb concentration in the blood. The blood analyzing device 100 of the present invention can obtain such an Hb concentration prior the hemostasis measurements. This means that the determined Hb parameter, such as total hemoglobin or at least one Hb fraction, can be used by the processor 140 when determining the viscosity representing value based on the detection signal. The relevant Hb parameter has previously been determined by the processor 140 and could be entered in the connected memory 150. Usage of the Hb parameter would allow the processor 140 to calculate a standardized viscosity representing value that is, for instance, normalized relative the Hb parameter for the same blood sample. Thus, the blood analyzing device 100 allows determination of normalized/ standardized values, which are not obtainable in a simple manner with the prior art techniques.

As was mentioned in the foregoing, the inducing means 200 of the blood analyzing device 100 preferably comprises a field applying means arranged for applying a field over at least a portion of the cuvette 20 in the sample container 10. This applied field affects the blood cells in the sample 30, either directly or indirectly, to induce a movement of the cells. In the former case, the field acts directly on the cells while in the latter case the field acts on material added to or originally present in the blood sample, which material causes a movement of the blood cells in the cuvette 20.

Figure 3A:
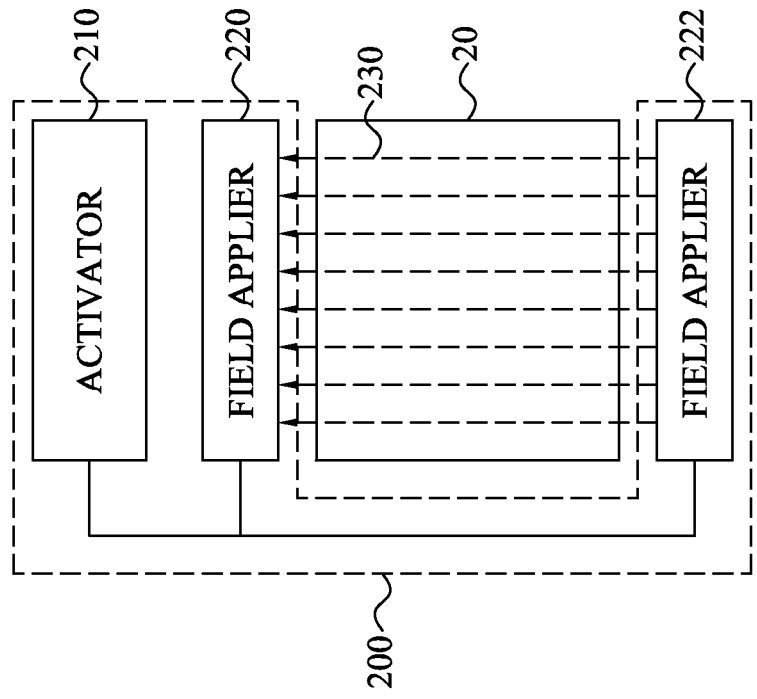
FIGS. 3A and 3B are schematic block diagrams of a movement inducing arrangement according to an embodiment of the present invention.
Figure 3B:
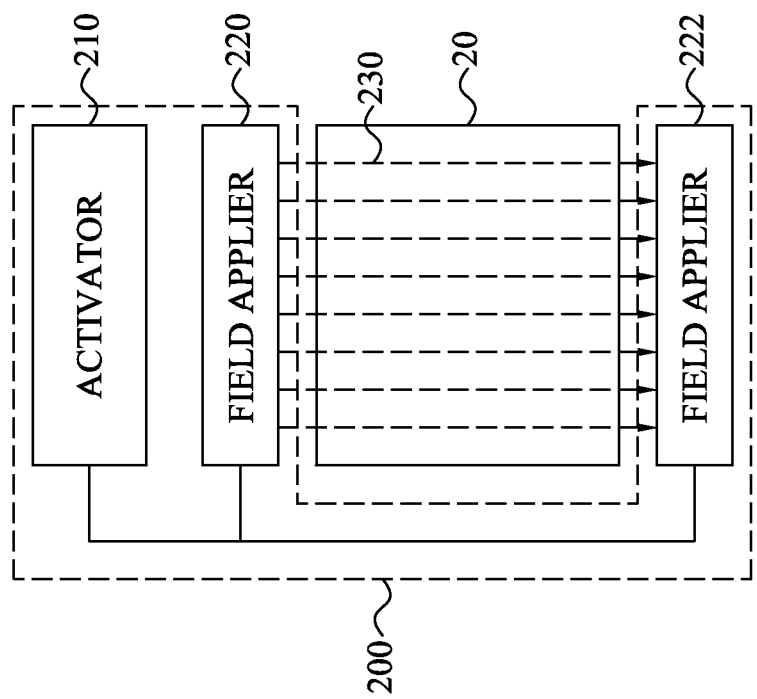
Figure 4D:
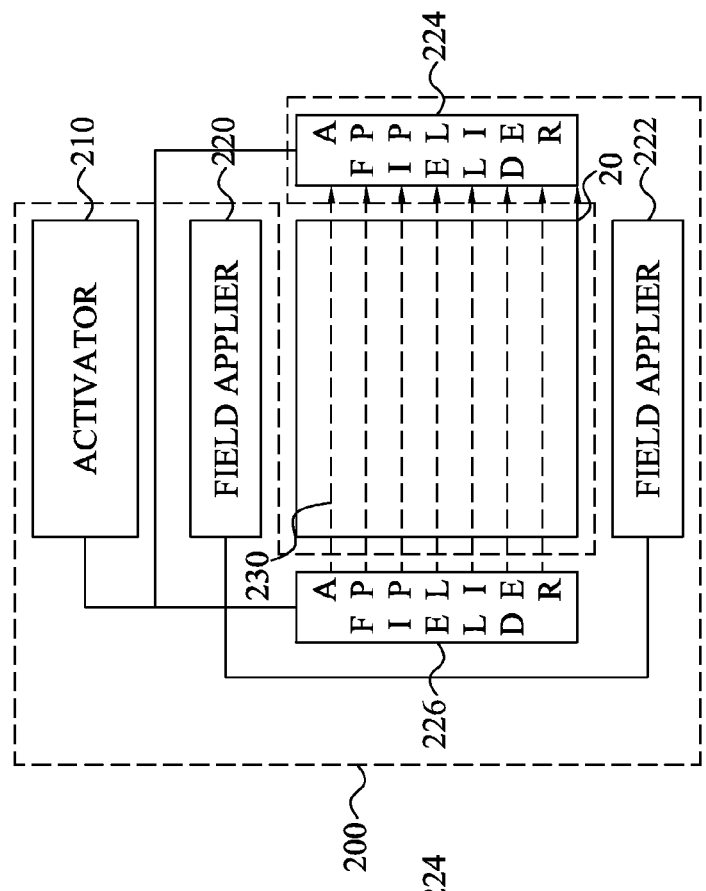
Figure 4C:
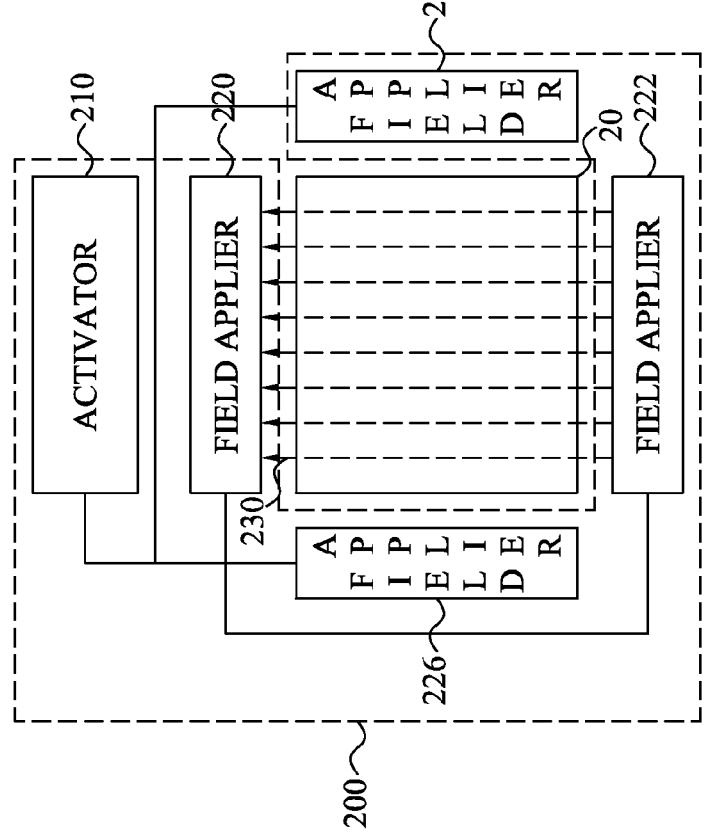

FIGS. 3A and 3B are illustrations of an embodiment of an inducing means 200 according to the present invention. The inducing means 200 comprises field applying means or field appliers 220, 222 arranged in connection to the cuvette 20 with the blood sample. The field appliers 220, 222 apply a field 230 over at least a portion of the cuvette 20 once activated by a field activator 210. The activator 210 is preferably arranged for triggering the field appliers 220, 222 to change the direction of the applied field 230, which is schematically illustrated by the figures. In FIG. 3A, the field 230 is directed from the upper applier 220 to the lower applier 222, while in FIG. 3B the field 230 has the opposite direction. This embodiment will induce a substantially linear movement of the blood cells in the cuvette 20.

FIGS. 4A to 4D illustrate another embodiment of an inducing means 200 having four field appliers 220, 222, 224, 226 arranged on either sides of the cuvette 20. The activator 210 of the inducing means 200 is preferably configured for alternatively activating pairs of the field appliers 220, 222, 224, 226 to thereby change the direction of the applied field 230 in a clockwise or counter-clockwise way. This field application causes a rotational movement of the blood cells in the cuvette.

In an alternative embodiment, a central field applier is arranged in the cuvette and is employed together with at least one peripheral field applier, preferably multiple peripheral field appliers as illustrated in FIGS. 4A to 4D, for providing a movement inducing field. In such a case, the applied field direction can be alternatively switched to induce a movement of red blood cells in the sample towards the cuvette center and out towards the periphery.

An embodiment of the inducing means 200 utilizes the negative surface charges present on the surface of the blood cells. In such a case, the field appliers 220, 222, 224, 226 applies an electrical field 230 across the blood sample to cause a movement of the blood cells in the opposite direction of the field 230, i.e. towards the positively charged applier. The field appliers 220, 222, 224, 226 can then be in the form of pairwise parallel plates connected to a voltage source of the activator 210. The activator 210 then applies a voltage over plates positioned on opposite sides of the cuvette 20 to form an electric field 230 between the plates.

As the blood cells aggregate or become intermeshed into the aggregate, the movement thereof in the blood sample given a specified, applied electric field strength ever more slow and sluggish due to the aggregation-causing viscosity increase. Depending on the field strength and the frequency of field direction changes, the aggregate of cells may actually accumulate in a portion of the cuvette and not be able to noticeably respond to the varying electric field without any changes in the field strength. The time of formation of such an aggregate can be used by the processor of the blood analyzing device as an aggregation representing value or parameter.

Thereafter, the activator 210 can increase the field strength of the applied electric field 230 to a second, comparatively higher, field strength. This higher field strength is selected anew to be able to induce a movement of the aggregating blood cells. The movement of the aggregation is followed by the detector as the field direction is varied by the activator 210. The hemostasis of the blood causes the formation of fibrin threads intermeshing or forming a network trapping blood cells to the aggregate. At this time point of the hemostasis even the second higher field strength is not strong enough to induce an unchanged movement of the blood cells due to the coagulation-caused further viscosity change. This time can be used by the processor as a coagulation representing value or parameter.

Figure 5:
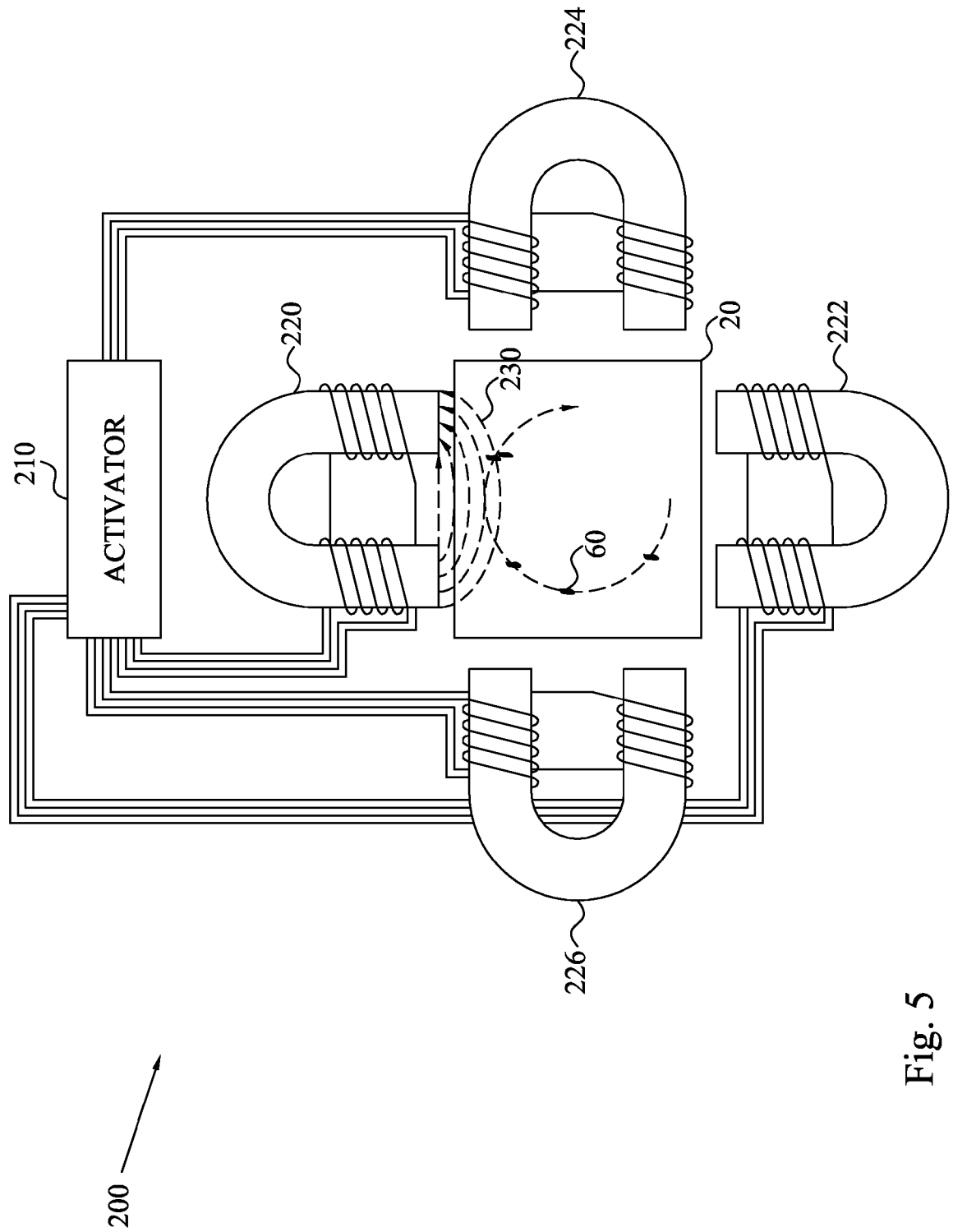
FIG. 5 is schematic block diagram of a movement inducing arrangement according to a further embodiment of the present invention.

FIG. 5 illustrates another embodiment of the inducing means 200 arranged in the blood analyzing device of the present invention. The inducing means 200 comprises field applying means 220, 222, 224, 226 arranged for applying a magnetic field 230 across at least a portion of the blood sample in the cuvette 20 to thereby induce a movement of the blood cells.

In this embodiment, one or more ferromagnetic objects 60 have been added to the sample prior, during or after filling the cuvette 20 with the blood. The ferromagnetic objects can be induced to move in the blood sample inside the cuvette by selectively activating and deactivating electromagnets 220, 222, 224, 226 positioned at different positions around the blood sample. The electromagnets 220, 222, 224, 226 are connected and controlled by an activator 210. The activator 210 is preferably not only able to switch on and off the electromagnets 220, 222, 224, 226 but also able to adjust the strength of an applied magnetic field, at least between a first and a second field strength level.

Prior any aggregation or coagulation, the ferromagnetic objects 60 can move relatively freely inside the blood sample.

However, during aggregation, the objects 60 become entrapped by the platelet-induced aggregations. As a consequence, movement becomes more restricted and may even stop when the viscosity has increased following the aggregation. The detector of the blood analyzing device can register and follow the movement of the blood cells in the sample as previously described. Alternatively, the ferromagnetic objects are instead followed as indirect markers of the blood cell movement.

The ferromagnetic objects 60 can be small iron objects, such as iron filing of a given or varying size, objects comprising a ferromagnetic core or coating, ferromagnetic or iron particles, grains or granulates. An alternative is to have a ferromagnetic needle hanging suspended in the cuvette 20 for allowing a rotational movement of the needle in the blood sample, similar to a compass needle. The activator 210 selectively switches, in this embodiment, on and off the multiple electromagnets 220, 222, 224, 226 in a clockwise or counterclockwise manner as positioned around the blood sample to induce a rotation of the thin ferromagnetic needle. As platelets and other blood cells aggregate, it becomes more difficult for the needle to rotate in the viscous blood sample. The aggregating cells may even become attached to the needle, thereby further preventing the rotation thereof in the magnetic field 230.

The detector may either be arranged for monitoring the change in absorbance or transmittance as aggregates of red blood cells are being moved through the detection volume, or monitoring the rotation of the ferromagnetic needle in the sample. The detection signal could be generated once the rotational speed has reduced below a predefined speed level. In such a case, the aggregation representing value is determined by processor based on the time period having elapsed for a defined starting point up to when the rotation speed falls below the threshold. In another embodiment, the detector is arranged for performing multiple detector readings in connection with a given time instance following the defined starting point. The processor utilizes these detector readings of the position of the needle at the different time instances to estimate a rotational speed of the needle at the given time instance. This estimated rotational speed is then used as a representation of the aggregation parameter by the processor.

Once the detection data required for estimating the aggregation parameter has been recorded, the activator 210 increases the field strength of the applied magnetic field 230 from the previously used first magnetic level to a second higher level that is useful for assessing the coagulation sub-process of hemostasis. This higher field strength anew induces a movement, preferably rotation, of the ferromagnetic object(s) 60 in the blood sample. As coagulation progresses, the viscosity of the blood increases further due to the presence of fibrin thread networks entrapping blood cells (and possibly the objects 60). The above described techniques for following the movement of the ferromagnetic objects 60, such as needle, during aggregation can also be used during this coagulation for determining a coagulation representing parameter or value based on the detection signal, e.g., time instance at a drop of rotational speed below a second threshold or estimated rotational speed at a given time instant.

Thus, the embodiment described above, and also the previous embodiment utilizing electric fields, can be used for both assessing the aggregation procedure and the platelet function of a blood sample and the coagulation procedure and cascade. This is a significant advantage over the prior art coagulation assessing solutions.

Figure 6:
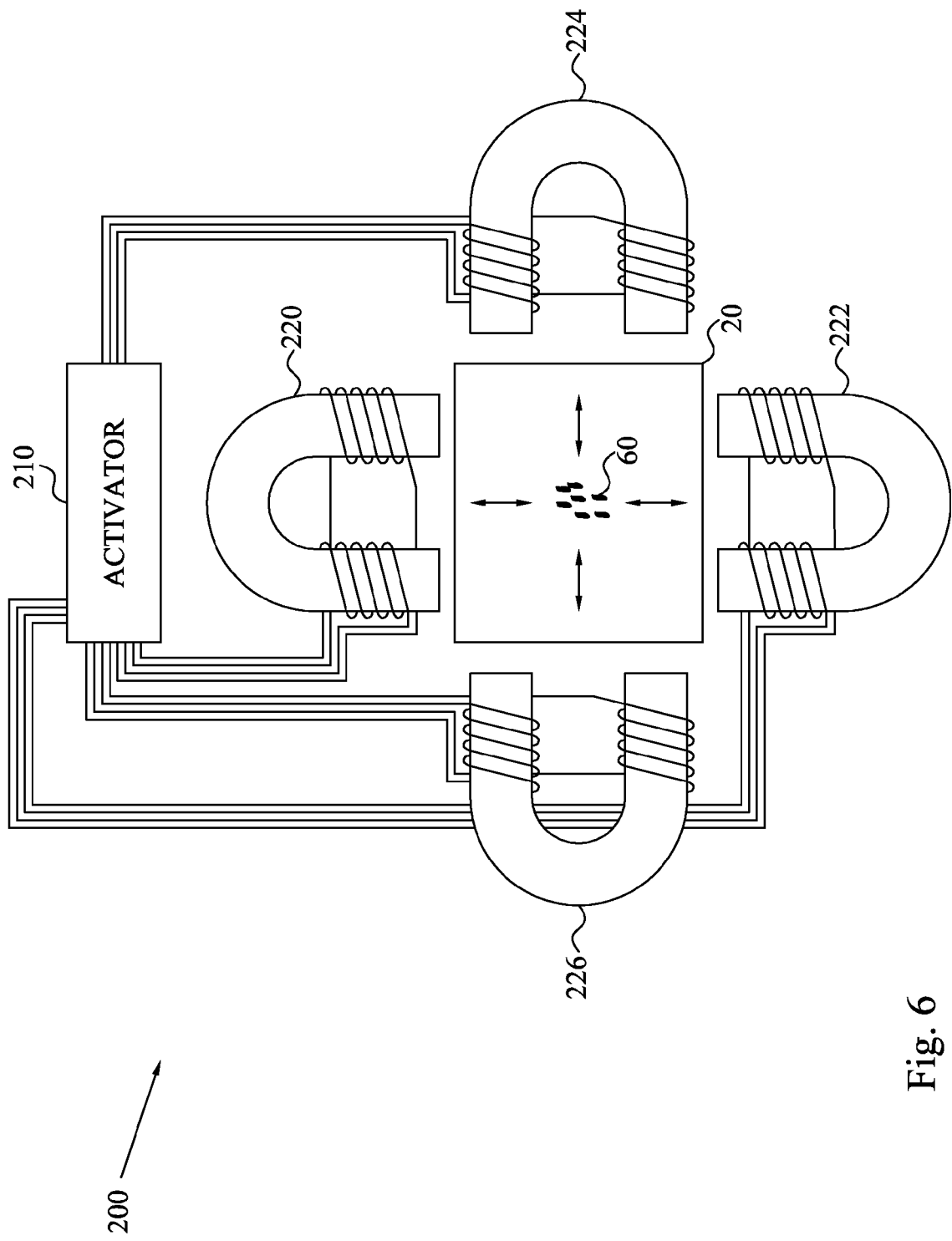
FIG. 6 is schematic block diagram of the movement inducing arrangement of FIG. 5 useful for coagulation efficiency monitoring.

The usage of magnetic fields and the addition of ferromagnetic objects have a further advantage in that the strength of a blood clot can be assessed by the blood analyzing device. FIG. 6 illustrates the inducing means 200 configured for blood clot analysis. In this case, the activator 210 preferably selectively switches direction of a magnetic field applied by electromagnets 220, 222; 224, 226 positioned on opposite sides of the blood sample in the cuvette 20. In addition, the field directions applied by the two opposite electromagnets 220, 222; 224, 226 are opposite. This causes an alternating stretching and pushing of the blood clot as at least some ferromagnetic objects 60 are entrapped in the clot. For instance, the magnetic field applied by the upper electromagnet 220 is at a given instance directed upwards in the figure simultaneously as the field of the opposite lower electromagnet 22 is directed downwards. This causes a stretching of the blood clot as some ferromagnetic objects 60 in the clot are drawn upwards while other are drawn towards lower electromagnet 222. The direction of the fields can then be changed to push the ferromagnetic objects together towards the center of the cuvette 20.

The speed of movement and/or the distance the ferromagnetic objects 60 can move during the alternating stretching-pushing action is registered by the detector and utilized by the processor for generating a parameter or value representative of the clot strength.

Thus, the field strength of the opposite electromagnets 220, 222; 224, 226 could be fixed during this clot strength analysis and then the movement of the ferromagnetic objects can be used for estimating the clot strength parameter. In an alternative embodiment, the field strength of the alternating magnetic field is increased continuously or stepwise and the detector registers the induced movement of the objects 60. The field strength that is able to achieve a minimum threshold movement of the objects 60 could instead or in addition be used as basis for the determination of the clot strength parameter.

Thus, in this embodiment a further analytical parameter of high diagnostic value is obtainable by the blood analyzing device of the invention.

Figure 7:
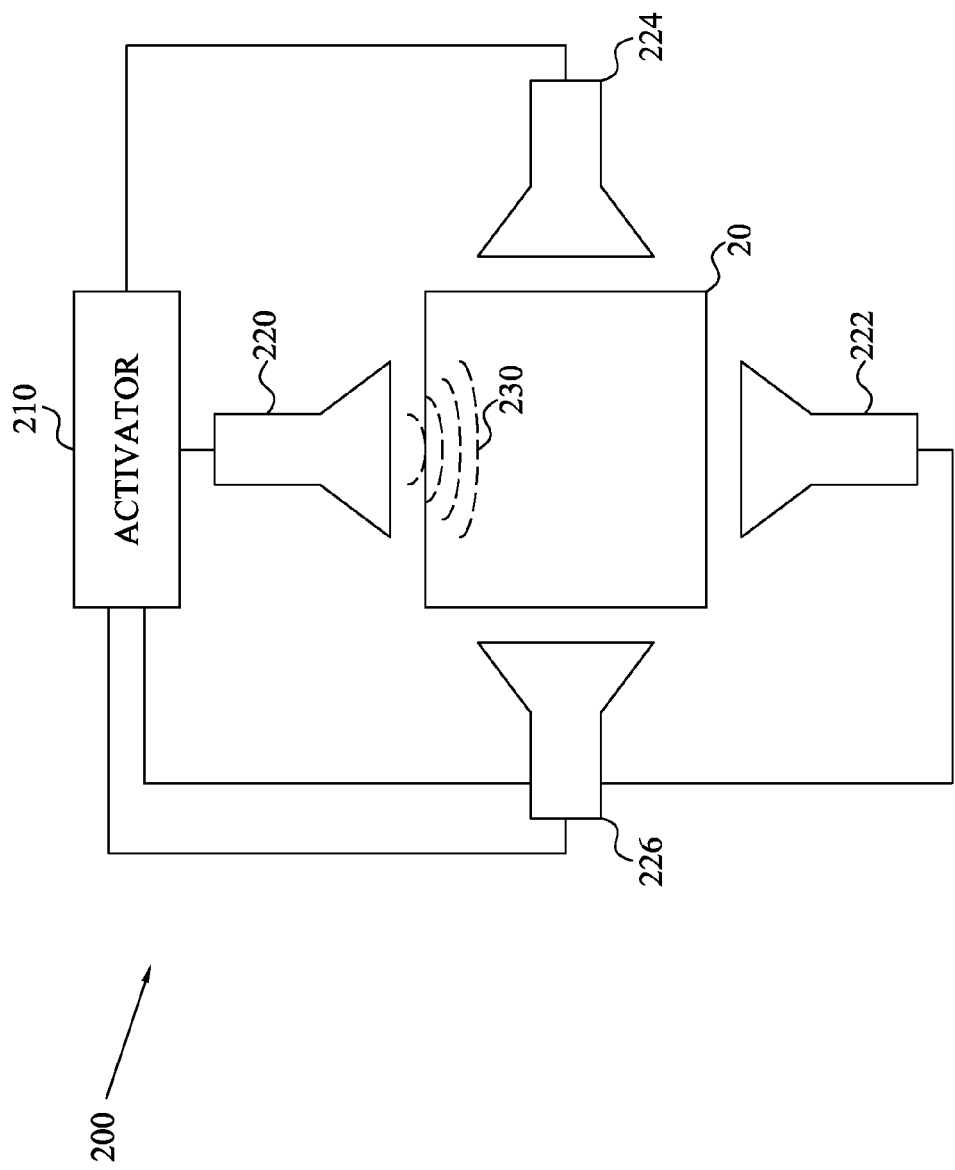
FIG. 7 is schematic block diagram of a movement inducing arrangement according to yet another embodiment of the present invention.

FIG. 7 illustrates another embodiment of the inducing means 200 implementable in the blood analyzing device of the invention. This inducing means 200 is arranged for applying pressure waves 230 into the blood sample to thereby induce movement of blood cells present therein. The inducing means 200 preferably comprises one or more ultrasound transducers 220, 222, 224, 226 positioned at different positions around the blood sample. An activator 210 is connected to the transducers for selectively activating/deactivating the transducers 220, 222, 224, 226 and preferably varying the amplitude and/or frequency of the applied ultrasound pressure waves 230. In similarity to previous embodiments, the transducers 220, 222, 224, 226 can be positioned around the cuvette 20 and be selectively activated by the activator 210 to apply pressure waves in a clockwise or counter-clockwise manner to thereby induce a rotational movement of the blood cells in the sample.

The inducing means 200 of FIG. 7 can also be utilized for assessing both the aggregation and coagulation function of the blood sample by, for the purpose of aggregation monitoring, utilizing a first amplitude and first frequency of the applied pressure waves. Once the aggregation data has been recorded by the detector, the activator can increase the amplitude of the pressure waves 230 to a second higher level and/or adjust the frequency to a second frequency level.

Figure 8:
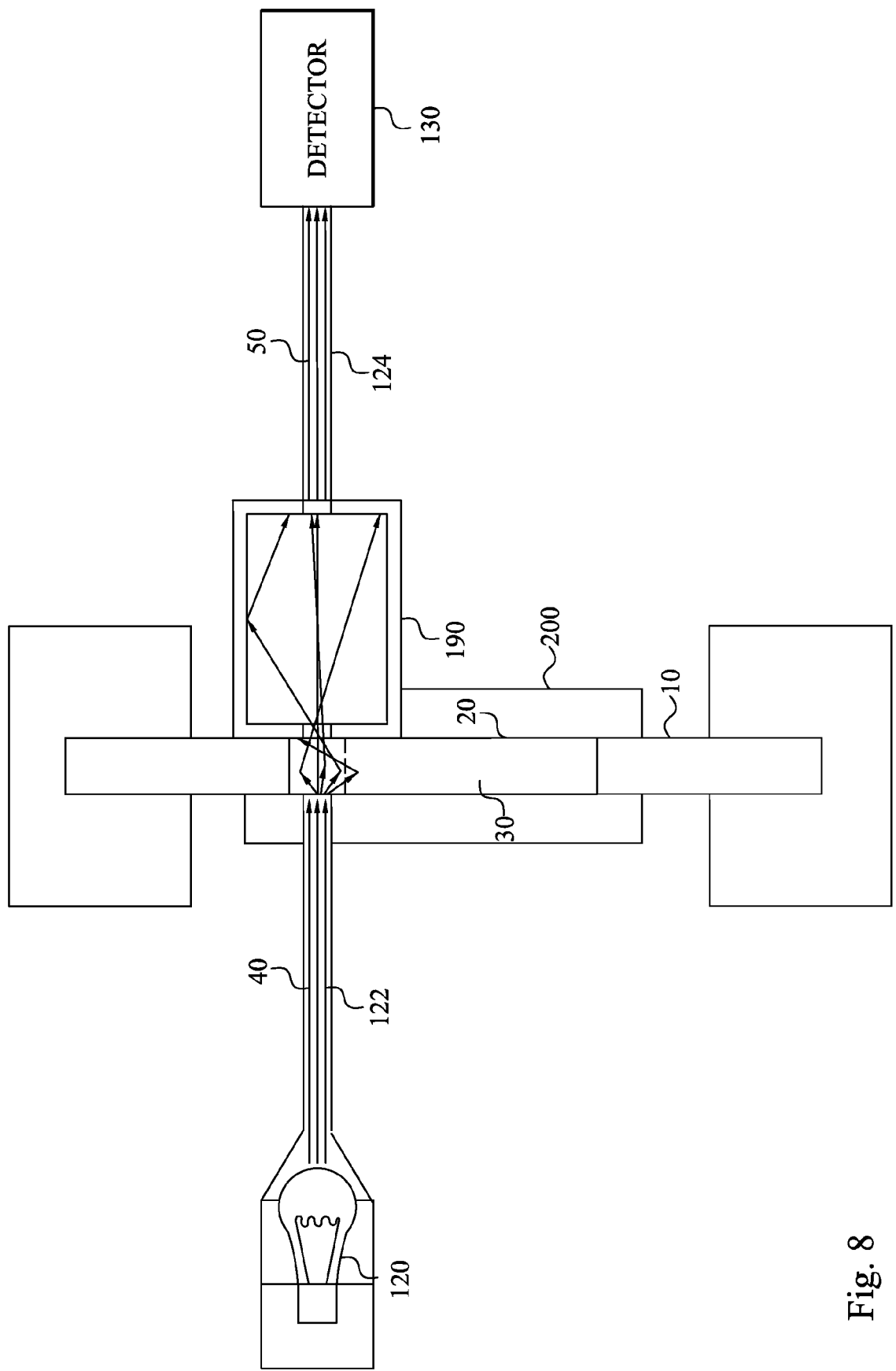
FIG. 8 schematically illustrates a portion of the light emitting, conducting and detecting path of the blood analyzing device according to an embodiment of the present invention.

FIG. 8 is a close-up view of a portion of the blood analyzing device of an embodiment of the present invention. The figure illustrates the light source 120 providing light to a measuring volume of the blood sample 30 in the cuvette 20. In this embodiment, an input light guide 122 is arranged for directing the input light 40 from the source 120 into the measuring volume. The light guide 122 can be in the form of an optical fiber or cable that is able to provide a parallel bundle of light rays towards the sample 30. As the light passes through the blood sample 30 it will collide with particles, e.g., blood cells. Some light will be absorbed and some will scatter and continue in different direction.

A light trap 190 can be arranged in connection with the side of the cuvette 20 opposite to the side at which the light enters the sample 30 from the light guide. This light trap 190 will reduce the amount of scattered, i.e., non-parallel light from the output light. Such a light trap 190 can be designed in the form of cylinder having non-reflective or light-absorbing inner walls. The diameters of the entry opening and the exit opening of the light trap 190 are smaller than the inner diameter of the cylinder. Furthermore, the length of the trap 190 could be in the range of 5 to 30 times the diameter of the entry and exit openings. The substantially parallel (non-scattering) output light 50 exits the light trap 190 and may be guided up to the light detector 130 by an output light guide 124. This can also be in the form of an optical fiber or cable. For more information of the usage of a light trap 190 and a blood analyzing device equipped with such a light trap 190 reference is made to the International patent application number WO 2006/104451, the teaching of which is hereby incorporated by reference.

The usage of such a light trap 190 is in particular advantageous for the purpose of Hb measurements. However, it can also be used, without any negative impact, on the hemostasis measurements. As a consequence, a blood analyzing device of the invention adapted for performing both Hb and hemostasis measurements in a same blood sample loaded in a cuvette 20 can advantageous be equipped with such a light trap 190.

The blood analyzing device of the present invention has several advantage diagnostic uses within the medical field. It is a valuable tool for detecting patients suffering from hemophilia, which is the name of a family of hereditary genetic disorders that impair the body's ability to control blood clotting or coagulation.

Today many patients having a history of cardiogenic diseases are prescribed anticoagulant medicines, such as warfarin-based drugs. These drugs are very hard to dose safely and accurately, requiring regular diagnostic tests for control and regulation. The present invention can be a simple tool in monitoring the coagulation function in these patients and thereby be used for assessing and/or controlling the prescription of anticoagulant medicines.

There are also several common active agents that affect and impair the aggregation and/or coagulation process when administered to a patient. For instance, acetylsalicylic acid or aspirin is one of the most frequently used drugs in the treatment of mild to moderate pain, including that of migraines and fever. Acetylsalicylic acid also has anti-platelet effect and is used in long-term, low doses to prevent heart attacks and blood clot formation in people at high risk for developing blood clots.

Blood banks manufacture so-called thrombocyte concentrates from blood drawn from donors. These concentrates are used in treating difficult cases of bleeding in connection with injuries or operations. There may be problems if the blood donors recently have been administered an anti-platelet drug, such as aspirin. There is therefore a need for a quick and cost effective device for measuring the thrombocytic activity in connection with blood donation as the quality of the thrombocyte concentration manufactured from the donated blood is of uttermost importance when treating critical cases.

It is statutory in many countries, that each blood donor should be tested with respect to hemoglobin (Hb) in connection with each donation occasion. The blood analyzing device of the present invention can be utilized for a Hb assessment in addition to the aggregation and/or coagulation analysis. The device of the invention is therefore advantageously used for analyzing blood that is to be used for thrombocyte concentration and other blood processing products.

The device embodiment of the invention that can be used for assessing the strength of a blood clot can advantageously be used before or during larger operations, such as orthopedic surgery, where it is important that the coagulation process functions correctly.

Diabetic patients often have small bleedings in capillaries with microscopic infarcts as a consequence. These microinfarcts have a tendency to be more frequent and/or severe over time, which is considered to be a consequence of a "trimming" of the coagulation process of the patient to a higher efficiency. The blood analyzing device of the present invention could be useful for monitoring the efficiency of the coagulation process based on the clot strength.

Figure 9:
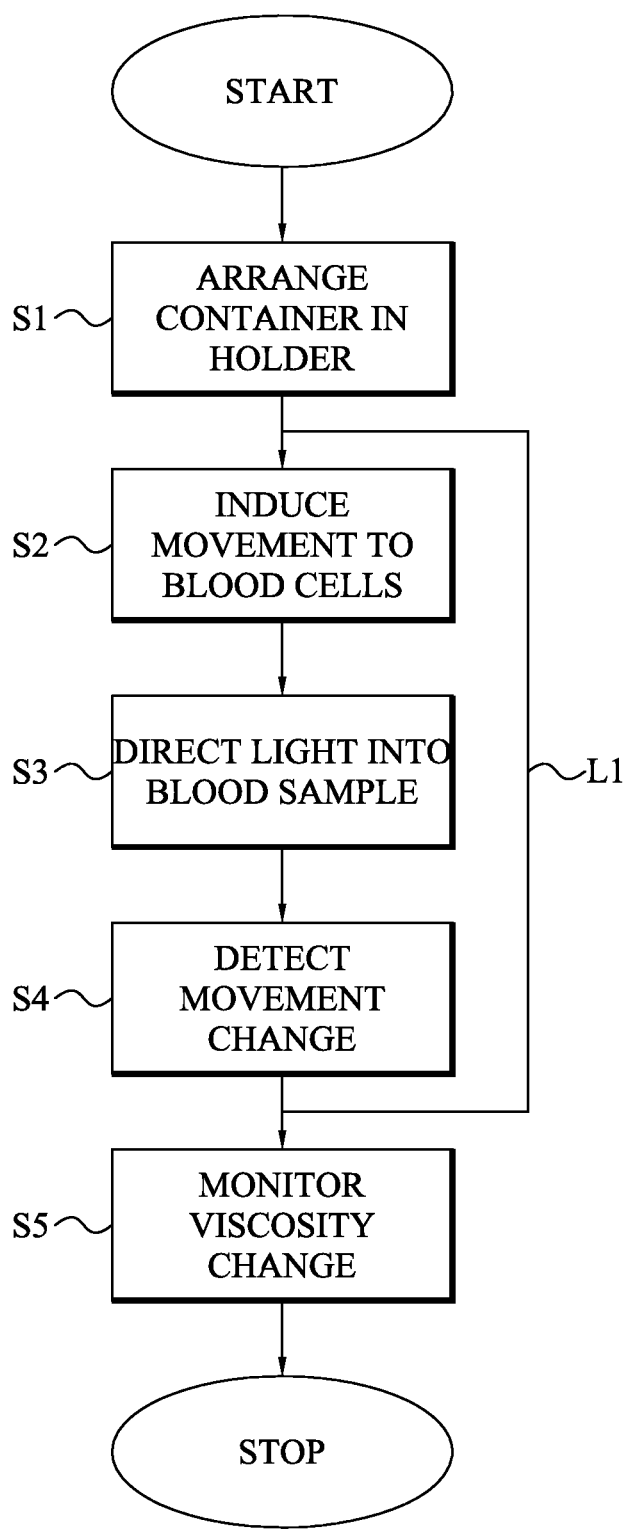
FIG. 9 is a flow diagram of a blood analyzing method according to an embodiment of the present invention.

FIG. 9 is a flow diagram of a method of analyzing a blood sample contained in a cuvette of a container according to the present invention. The method starts in step S1, where the container is arranged in a holder of a blood analyzing device according to the present invention. A next step S2 induces a movement of blood cells in the sample, preferably by applying a field over at least a portion of the sample. In a next step S3, light is guided from the light source into the blood sample. The light is allowed to pass through the blood sample in the cuvette and the resulting output light is detected in step S4. Thus, the movement of the blood cells is monitored based on the output light to detect a change in the induced movement caused by a hemostasis process leading an increase in viscosity of the sample, preferably based on a change, i.e., reduction, in the rate of change of absorbance/transmittance caused by the movement of red blood cell aggregates past the detection window or volume. A detection signal is generated based on the detected change in induced movement and is used for monitoring the viscosity change in step S5.

The inducing step S2, light directing step S3 and the detecting step S4 can preferably be performed continuously, periodically or at least intermittently during the analyzing period, which is schematically illustrated by the line L1. For instance, the movement can be induced by varying the direction of the movement inducing field to obtain a desired movement pattern, such as a rotational movement. In such a case, field appliers can be actively switched on and off according to a predetermined scheme to achieve the varying field directions.

The detector preferably performs detection sampling at a defined frequency to thereby be able to accurately detect a sudden change in the cell movement due to aggregation or coagulation.

The light detection can also be used for Hb measurements. In such a case, the detected light is preferably non-scattering light obtained by guiding the output light into a light trap before being detected by a light detector. At least one of total Hb concentration or the concentration of at least one Hb fraction in the blood sample based on the light detected. As has been previously discussed, the hemostasis determination can be performed at least partly based on the determined Hb value.

Figure 10:
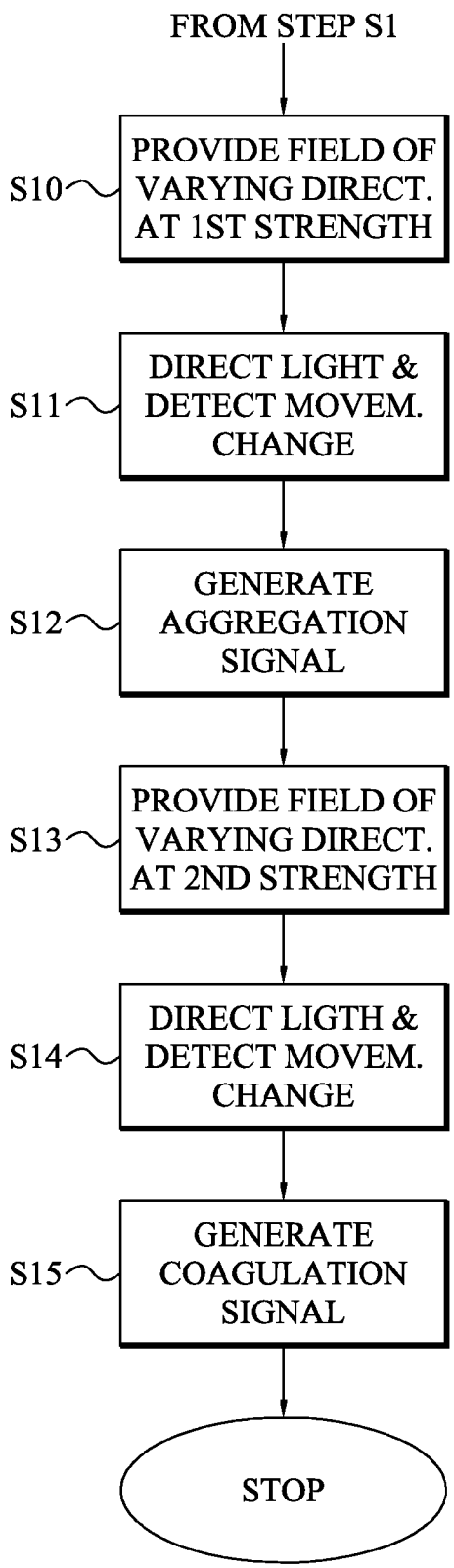
FIG. 10 is a flow diagram illustrating an embodiment of the inducing, detecting and monitoring steps of the blood analyzing method of FIG. 9.

FIG. 10 is a flow diagram illustrating a possible implementation of the inducing detecting and monitoring steps of the blood analyzing method in FIG. 9. The method continues from step S1 of FIG. 9. In a next step S10, a field of a first field strength is provided over at least a portion of the blood sample contained in the cuvette to induce the movement of the blood cells. The field can be an electric field affecting the negative charges on the red blood cells. Alternatively, the field can be a magnetic field affecting ferromagnetic object(s) present in the cuvette, which impart(s) movement to the blood cells therein. Also an acoustic field can be used by applying (ultrasound) pressure waves into the blood sample. The field is preferably a varying field in that the direction of the field is varied to achieve a desired linear or rotational movement of the blood cells in the cuvette.

Light is directed into the blood sample and the detector monitors the field-induced movement of the blood cells and detects, in step S11 and based on the output light, a change in the movement due to an increase in the blood viscosity originating from the aggregation process of hemostasis. The processor of the analyzing device generates an aggregation signal or parameter based on the detection signal in step S12. This parameter is thus representative of the thrombocyte activity of the blood and the aggregation process. The parameter could, for instance, indicate the time until the detected aggregation-caused movement change occurs. This means that a low parameter value corresponds to a high thrombocyte activity and vice versa.

Once aggregation has occurred is assessed by the device, the field strength of the (electric, magnetic or acoustic) field is increased in step S13 from the first level to a second higher level to combat the viscosity increase and once more induce movement in the blood sample. Also this field is preferably applied by varying the field direction during the movement monitoring. The detector detects in step S14 based on the directed light when the coagulation of the hemostasis increases the viscosity further in the sample and there is a significant change in the induced movement of the blood cells. The processor generates a coagulation signal in step S15 based on the movement change detection of step S14. This coagulation signal or parameter is representative of the coagulation efficiency of the blood sample and could indicate the time up to the change in induced movement occurring due to the coagulation-based viscosity increase. The method ends.

Figure 11:
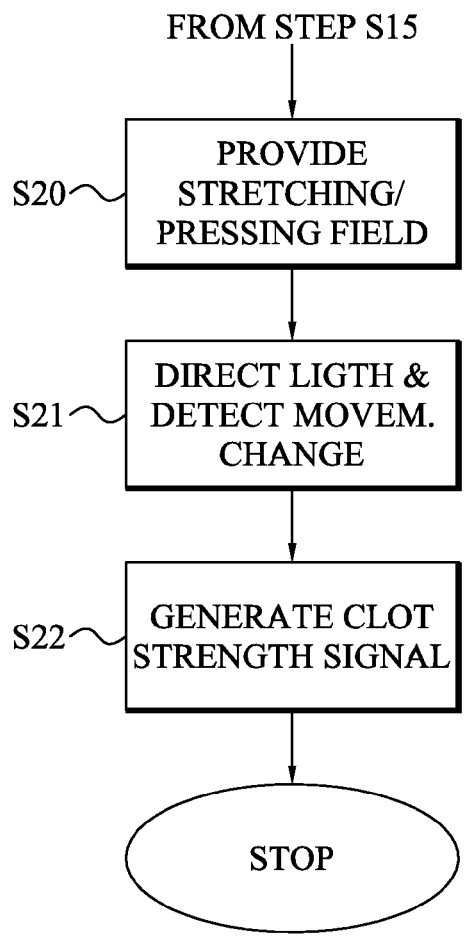
FIG. 11 is a flow diagram illustrating additional steps of the blood analyzing method of FIG. 10.

If the applied field is a magnetic field and small ferromagnetic objects have been added to the blood sample, also the clot strength can be assessed according to the invention. The method then continues from step S15 of FIG. 10 and continues to step S20 of FIG. 11. This step S20 involves providing an alternating stretching and pressing field by alternating the direction of the magnetic field of two electromagnets positioned on opposite sides of the blood sample. The alternating field operates on the ferromagnetic objects that are entrapped in the formed blood clot. The movement of these objects is monitored in step S21 and the monitoring is used in step S22 for generating a signal or parameter representative of the clot strength. This parameter is also of diagnostic value for assessing the coagulation efficiency of the blood. The parameter can be representative of the field strength required for achieving a defined stretching and pushing action. Alternatively, the time until a given such stretching and pushing action could be used as clot strength parameter. The method then ends.

It will be understood by a person skilled in the art that various modifications and changes may be made to the present invention without departure from the scope thereof, which is defined by the appended claims.

The invention claimed is:

1. A blood analyzing device comprising:
  a holder arranged for carrying a container having a cuvette comprising a blood sample;
  a unit for inducing movement of blood cells in said blood sample when said container is positioned in said holder;
  a light source arranged for providing input light of a wavelength at which a hemoglobin species has maximum absorbance into said blood sample;
  a detector arranged for i) detecting, at least once within a measuring time interval following positioning of said container in said holder, output light having passed through said blood sample, ii) detecting, based on said output light from said blood sample and following said measuring time interval, a change in said induced movement of said blood cells in said blood sample as a reduction in a rate of change of absorbance at said wavelength at which said hemoglobin species has maximum absorbance and iii) generating a detection signal based on said detected change in said induced movement; and
  a processor connected to said detector and configured to i) determine at least one of total hemoglobin or at least one hemoglobin fraction in said blood sample based on said output light detected during said measuring time interval and ii) determine a viscosity representing signal representative of a viscosity change in said blood sample based on said detection signal and said at least one of total hemoglobin or at least one hemoglobin fraction.

2. The device according to claim 1, wherein said unit for inducing movement comprises a field applier arranged for applying a field of varying direction across said blood sample to induce movement of said blood cells in said blood sample.

3. The device according to claim 2, wherein said field applier is arranged for applying an electrical field of varying direction across said blood sample to induce movement of said blood cells in said sample.

4. The device according to claim 2, wherein said field applier is arranged for applying a magnetic field of varying direction across said blood sample to induce movement of said blood cells in said blood sample.

5. The device according to claim 4, wherein said field applier comprises:
  a set of multiple electromagnets positioned at different positions around said blood sample when said container is positioned in said holder; and
  a field activator arranged for selectively activating said multiple electromagnets to provide said magnetic field of varying direction across said blood sample.

6. The device according to claim 5, wherein said field activator is arranged for selectively switching on and off said multiple electromagnets in a clockwise or counter-clockwise manner as positioned around said blood sample.

7. The device according to claim 4, wherein said cuvette comprises said blood sample and ferromagnetic objects suspended in said blood sample and said field applier comprises:
  a set of multiple electromagnets positioned at different positions around said blood sample when said container is positioned in said holder; and
  a field activator arranged for selectively activating said multiple electromagnets and selectively switching direction of a first magnetic field applied by a first electromagnet of a pair and selectively switching direction of a second magnetic field applied by a second electromagnet of said pair, said first electromagnet and said second electromagnetic are positioned on either sides of said blood sample and said direction of said first magnetic field being opposite to said direction of said second magnetic field.

8. The device according to claim 7, wherein said field activator is arranged for increasing a field strength of said first magnetic field and second magnetic field, said detector is arranged for detecting a stretching-pressing movement of a blood clot in said blood sample induced by said pair of electromagnets, and said processor is arranged for generating a clot strength signal based on a field strength of at least one of said first magnetic field and said second magnetic field when said detector detects said stretching-pressing movement and based on said at least one of total hemoglobin or at least one hemoglobin fraction.

9. The device awarding to claim 2, wherein said field applier is arranged for initially applying said field at a first field strength and for applying said field at a second field strength following a detection of a viscosity change in said blood sample caused by aggregation of thrombocytes in said blood sample, said second field strength being larger said first field strength.

10. The device according to claim 9, wherein said processor is configured to generate an aggregation detection signal based on detection of a predefined change in viscosity of said blood sample as determined based on said detection signal and said at least one of total hemoglobin or at least one hemoglobin fraction, said field applier is responsive to said aggregation detection signal and switches from said first field strength to said second field strength upon reception of said aggregation detection signal.

11. The device according to claim 9, wherein said processor is configured to generate a coagulation detection signal based on detection of a predefined change in viscosity of said blood sample as determined based on said detection signal and said at least one of total hemoglobin or at least one hemoglobin fraction, said predefined viscosity change being detectable following said field applier switching to said second field strength.

12. The device according to claim 2, wherein said field applier is arranged for applying pressure waves of varying direction into said blood sample to induce movement of said blood cells in said blood sample.

13. The device according to claim 12, wherein said field applier is arranged for initially applying said pressure waves at with a first amplitude and at a first frequency and for applying said pressure waves at a second amplitude and/or at a second frequency following a detection of a viscosity change in said blood sample caused by aggregation of thrombocytes in said blood sample.

14. The device according to claim 13, wherein said processor is configured to generate an aggregation detection signal based on detection of a predefined change in viscosity of said blood sample as determined based on said detection signal and said at least one of total hemoglobin or at least one hemoglobin fraction, said field applier is responsive to said aggregation detection signal and switches from said first amplitude and said first frequency to said second amplitude and/or said second frequency upon reception of said aggregation detection signal.

15. The device according to claim 13, wherein said processor is configured to generate a coagulation detection signal based on detection of a predefined change in viscosity of said blood sample as determined based on said detection signal and said at least one of total hemoglobin or at least one hemoglobin fraction, said predefined viscosity change being detectable following said field applier switching to said second amplitude and/or said second frequency.

16. The device according to claim 12, wherein said field applier comprises:
a set of multiple ultrasound transducers positioned at different positions around said blood sample when said container is positioned in said holder; and
a field activator arranged for selectively activating said multiple ultrasound transducers to provide ultrasound pressure waves of varying direction across said blood sample.

17. The device according to claim 16, wherein said field activator is arranged for selectively switching on and off said multiple ultrasound transducers in a clockwise or counter-clockwise manner as positioned around said blood sample.

18. A method of analyzing a blood sample contained in a cuvette of a container, said method comprising: arranging said container in a holder of a blood analyzing device;
providing input light from a light source of a wavelength at which a hemoglobin species has maximum absorbance into said blood sample;
detecting, at least once within a measuring time interval following positioning of said container in said holder, output light having passed through said blood sample;
determining at least one of total hemoglobin or at least one hemoglobin fraction in said blood sample based on said output light detected during said measuring time interval;
inducing movement of blood cells in said blood sample;
detecting, based on said output light from said blood sample and following said measuring time interval, a change in said induced movement of said blood cells in said blood sample as a reduction in a rate of change of absorbance at said wavelength at which said hemoglobin species has maximum absorbance;
generating a detection signal based on said detected change in said induced movement; and
determining a viscosity representing signal representative of a viscosity change in said blood sample based on said detection signal and said at least one of total hemoglobin or at least one hemoglobin fraction.

19. The method according to claim 18, wherein inducing said movement comprises providing a field of varying direction across said blood sample to induce movement of said blood cells in said blood sample.

20. The method according to claim 19, wherein providing said field comprises providing a magnetic field of varying direction across said blood sample to induce movement of said blood cells in said blood sample.

21. The method according to claim 20, further comprising: suspending ferromagnetic objects in said blood sample;
selectively switching direction of a first magnetic field applied by a first electromagnet of a pair; and
selectively switching direction of a second magnetic field applied by a second electromagnet of said pair, said first electromagnet and said second electromagnetic are positioned on either sides of said blood sample and said direction of said first magnetic field being opposite to said direction of said second magnetic field.

22. The method according to claim 21, further comprising:
increasing a field strength of said first magnetic field and second magnetic field;
detecting a stretching-pressing movement of a blood clot in said blood sample induced by said pair of electromagnets; and
generating a clot strength signal based on a field strength of at least one of said first magnetic field and said second magnetic field when said stretching-pressing movement is being detected.

23. The method according to claim 19, wherein providing said field comprises:
- initially providing said field at a first field strength;
- providing said field at a second field strength following a detection of a viscosity change in said blood sample caused by aggregation of thrombocytes in said blood sample, said second field strength being larger said first field strength, wherein determining said viscosity representing signal comprises generating an aggregation detection signal based on detection of a predefined change in viscosity of said blood sample as determined based on said detection signal, and providing said field at said second field strength is performed in response to said aggregation detection signal and said at least one of total hemoglobin or at least one hemoglobin fraction.

24. The method according to claim 19, wherein providing said field comprises:
- initially providing said field at a first field strength;
- providing said field at a second field strength following a detection of a viscosity change in said blood sample caused by aggregation of thrombocytes in said blood sample, said second field strength being larger said first field strength, wherein
- determining said viscosity representing signal comprises generating a coagulation detection signal based on detection of a predefined change in viscosity of said blood sample as determined based on said detection signal and said at least one of total hemoglobin or at least one hemoglobin fraction, said predefined viscosity change being detectable following application of said second field strength.

25. The method according to claim 19, wherein providing said field comprises applying pressure waves of varying direction into said blood sample to induce movement of said blood cells in said blood sample.

26. The method according to claim 25, wherein applying said pressure waves comprises:
- initially applying said pressure waves at with a first amplitude and at a first frequency; and
- applying pressure waves at a second amplitude and/or at a second frequency following a detection of a viscosity change in said blood sample caused by aggregation of thrombocytes in said blood sample, wherein determining said viscosity representing signal comprises generating an aggregation detection signal based on detection of a predefined change in viscosity of said blood sample as determined based on said detection signal and said at least one of total hemoglobin or at least one hemoglobin fraction, and applying said pressure waves at said second amplitude and/or said second frequency is performed in response to said aggregation detection signal.

27. The method according to claim 25, wherein applying said pressure waves comprises:
- initially applying said pressure waves at with a first amplitude and at a first frequency; and
- applying pressure waves at a second amplitude and/or at a second frequency following a detection of a viscosity change in said blood sample caused by aggregation of thrombocytes in said blood sample, wherein determining said viscosity representing signal comprises generating a coagulation detection signal based on detection of a predefined change in viscosity of said blood sample as determined based on said detection signal and said at least one of total hemoglobin or at least one hemoglobin fraction, said predefined viscosity change being detectable following applying said pressure waves at said second amplitude and/or said second frequency.

\* \* \* \* \*